United States Patent [19]
Mathre et al.

[11] Patent Number: 5,760,249
[45] Date of Patent: Jun. 2, 1998

[54] SYNTHESIS OF HYDROXYSULFONE AND RELATED COMPOUNDS

[75] Inventors: David J. Mathre, Skillman; Paul Sohar, Warren, both of N.J.; David Moody, Fife, Scotland; Andrew J. Blacker, North Rigton, United Kingdom

[73] Assignees: Merck & Co., Inc., Rahway, N.J.; Zeneca Limited, London, United Kingdom

[21] Appl. No.: 704,195

[22] Filed: Aug. 28, 1996

Related U.S. Application Data

[60] Provisional application No. 60/002,890 Aug. 29, 1995.

[51] Int. Cl.$^6$ ............................................. C07D 495/04
[52] U.S. Cl. ............................................. 549/23; 204/157.7
[58] Field of Search ............................ 549/23; 204/157.7

[56] References Cited

U.S. PATENT DOCUMENTS

| | | | |
|---|---|---|---|
| 4,797,413 | 1/1989 | Baldwin et al. | 514/432 |
| 4,968,814 | 11/1990 | Blacklock et al. | 549/66 |
| 4,968,815 | 11/1990 | Blacklock et al. | 549/66 |
| 5,574,176 | 11/1996 | Mathre et al. | 549/66 |

FOREIGN PATENT DOCUMENTS 0 617 037 A1  9/1994  European Pat. Off.

OTHER PUBLICATIONS

T.K. Jones, et al, *J. Org. Chem.*, 56(2), pp. 763—769 (1991).

D. J. Mathre, et al., *J. Org. Chem.*, 58, pp. 2880–2888 (1993).

Blacklock, et al., *J Org Chem*; 57, pp. 1672–1679 (1993).

*Primary Examiner*—Richard L. Raymond
*Attorney, Agent, or Firm*—Sylvia A. Ayler; Mark R. Daniel

[57] ABSTRACT

This invention is concerned with an improved process for the synthesis of hydroxysulfone, which is a key intermediate in the synthesis of carbonic anhydrase inhibitors, especially dorzolamide. Carbonic anhydrase inhibitors are known to be effective in treating elevated intraocular pressure or glaucoma.

10 Claims, No Drawings

SYNTHESIS OF HYDROXYSULFONE AND RELATED COMPOUNDS

This application claims the benefit of provisional application U.S. Ser. No. 60/002,890 filed Aug. 29, 1995.

BACKGROUND OF THE INVENTION

The current therapy for control of elevated intraocular pressure (IOP) or ocular hypertension which is believed to be a factor in the onset and progress of glaucoma is typically effected with a variety of topically applied agents which fall within four categories: β-blockers, sympathomimetic agents, parasympatho-mimetic agents and cholinesterase inhibitors. The adjuvant oral administration of a carbonic anhydrase inhibitor (CAI) is practiced when the above-described topical agent's side effects limits its use and/or it fails to achieve adequate IOP control. The orally active CAI's can exhibit serious side-effects such as anorexia, gastrointestinal upset and parasthesias. Therefore an intense and ongoing search has been mounted for a topically active CAI that would not exhibit such side effects due to the route of administration and inherent target organ specificity. This search has resulted in the discovery of a class of compounds by Baldwin et al. (U.S. Pat. No. 4,797,413) of general formula:

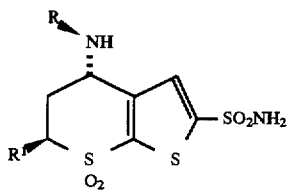

wherein R and $R^1$ are lower alkyl, especially dorzolamide, wherein R is ethyl and $R^1$ is methyl.

U.S. Pat. No. 4,797,413 discloses a process for preparing the racemic modification of the alkyl 3-(thien-2-ylthio) butyrate and its homologs. The prior art process comprises addition of the 2-thienyl-thiol (II) across the double bond of a substituted acrylic acid (IV) to yield acid I:

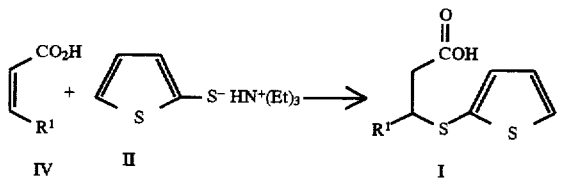

followed by synthesis of the final diastereomeric product, the isomers of which must be separated and each resolved to obtain the most active (S,S)-enantiomer. The isomer separations result in an automatic loss of the bulk of the chemical product.

U.S. Pat. No. 4,968,815 discloses a process for preparing the acid of structural formula I:

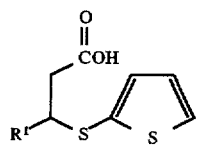

which comprises treating a nucleophile of structure II with a compound of structure III as shown:

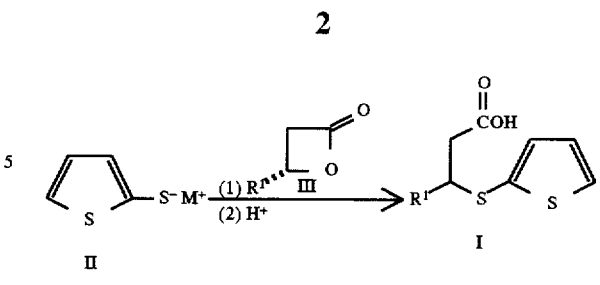

wherein the R groups are as hereinafter defined U.S. Pat. No. 4,968,814 and Blacklock et al., J. Org. Chem., 1993, 58, 1672–1679 also teaches a process for preparing the chiral intermediate formula I. However, these prior art processes involve many steps, employ heavy metal oxidants and are expensive and very time consuming.

It is therefore an object of this invention to provide a process for the synthesis of a hydroxysulfone which is more economical than previously possible and eliminates the use of heavy metal oxidants.

SUMMARY OF THE INVENTION

This invention is concerned with an improved process for the synthesis of a hydroxysulfone of structural formula III

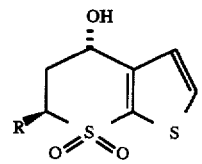

wherein R is hydrogen, $C_{1-4}$ alkyl, or $C_{1-4}$ alkoxy-$C_{1-4}$alkyl. The hydroxysulfone is a key intermediate in the synthesis of the compound of formula V:

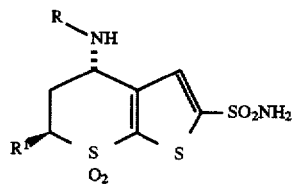

wherein R and $R^1$ are lower alkyl, especially dorzolamide, wherein R is ethyl and $R^1$ is methyl, a carbonic anhydrase inhibitor topically effective in the treatment of ocular hypertension and glaucoma.

The instant process reduces the reaction to a single batch process and eliminates the use of heavy metal oxidants, while retaining the high enantiomeric purity of the product.

DETAILED DESCRIPTION OF THE INVENTION

The novel process of the present invention can be depicted as shown in Scheme I below:

SCHEME 1

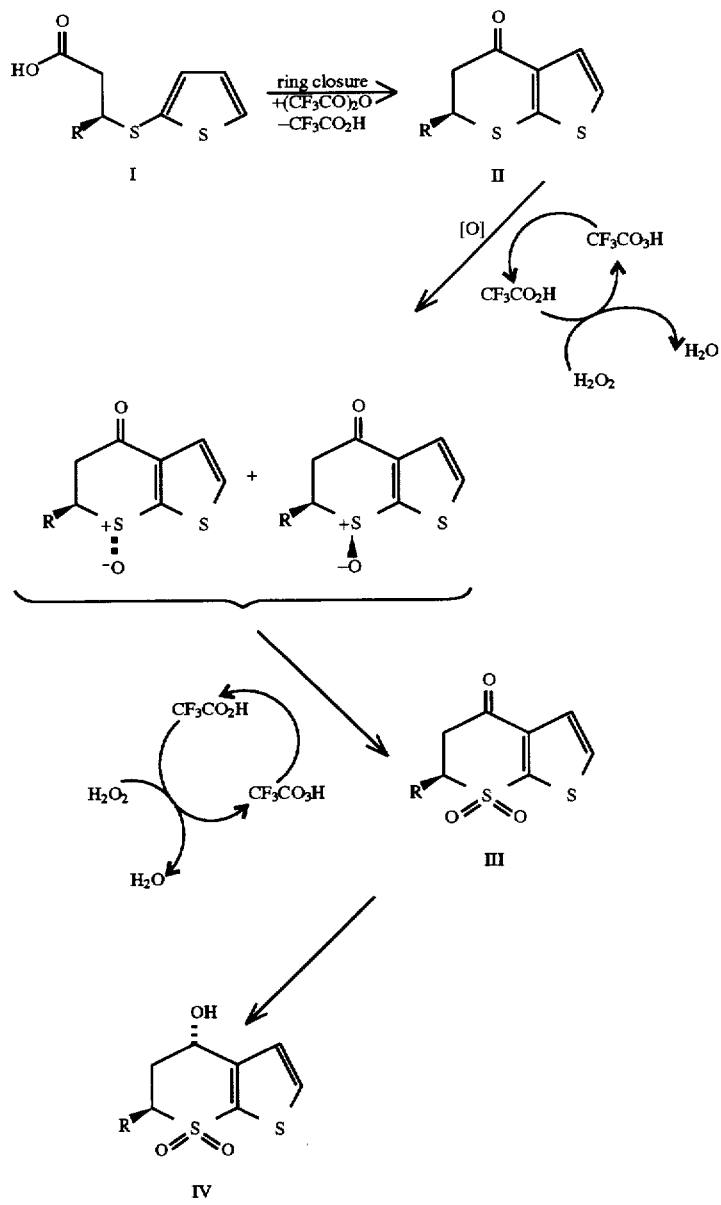

Preparation of a Compound of structural formula IV:

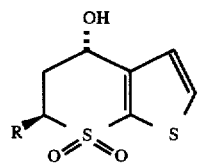

wherein R is hydrogen, $C_{1-4}$ alkyl, or $C_{1-4}$ alkoxy-$C_{1-4}$ alkyl, comprises adding to a solution containing a solvent, belonging to a group consisting of toluene, benzene, cyclohexane, heptane, xylene, and the like, preferably toluene and a compound of formula I:

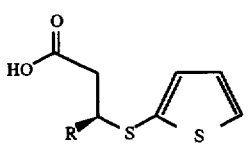

wherein R is described as above, an anhydride belonging to the group consisting of trifluoroacetic anhydride, acetic anhydride, trichloroacetic anhydride, and the like, and mixtures thereof, preferably trifluoroacetic anhydride, all optionally in the presence of acids such as carboxylic acids or inorganic acids, preferably phosphoric, polyphosphoric, orthophosphoric acids, or phosphorus pentoxide, while maintaining a temperature of about −5° to about 50° C., preferably from about 20° C. to about 40° C., and most preferably from about 25° C. to about 35° C., for about 1 to about eight hours to produce a solution containing a compound of structural formula II:

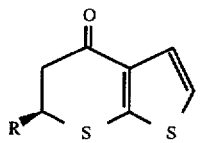

wherein R is described above. Any excess anhydride unused in the reaction is hydrolyzed by addition of a small amount of water, preferably from about 0.2 to about 2 equivalents of the original anhydride employed, prior to the addition of the oxidizing agent. To this solution is added at least about 2 mole equivalents and preferably from about 2 to about 4 mole equivalents of an oxidizing agent belonging to a group consisting of hydrogen peroxide, t-butyl hydroperoxide periodate, perchlorate electrochemical oxidation and the like, preferably hydrogen peroxide, while maintaining a temperature of about 15° C. to 80° C., preferably about 20° C. to about 60° C., for about 1 to about 32 hours, preferably from about 2 to about 12 hours and most preferably from about 4 to about 8 hours, to produce Compound III,

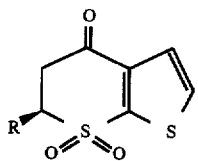

wherein R is described above, reducing Compound III to produce Compound IV and isolating compound IV.

The oxidation of the sulfide to the sulphoxide to the sulfone is performed directly after the ring closure by addition of the oxidizing agent (i.e., the cyclization and oxidation reaction are coupled in a single step). The reaction mixture at this point contains a byproduct from the previous reaction, the carboxylic acid. The oxidizing agent oxidizes the acid to the peracid, which then effects oxidation of the sulfide to the sulphoxide to the sulfone. A feature of this invention is that a reagent already present in the reaction mixture is converted to a suitable oxidizing agent and the need for a heavy metal oxidant is eliminated.

The reduction can be carried out by methods known to those skilled in the art. For example, Compound III can be reduced by subjecting it to the action of a microorganism such as Ambrosiozyma, Arthroascus Rhodotorula, Saccharomycopsis, Trichosporon and the like, which reduces the oxygen atom of carbonyl group at the 4-position of the thienothiopyran ring to the hydroxyl group. Chemical reducing agents can also be used. These include lithium aluminum hydride, diisobutyl aluminum hydride, aluminum hydride, lithium aluminum, tri-t-butoxy hydride, diborane, and the like.

The reaction can be quenched by addition of the reaction mixture or part of the reaction mixture, preferably the aqueous oxidizing phase of a biphasic solution to aqueous ethyl acetate, or aqueous sodium sulphite or bisulphite or addition of aqueous ethyl acetate to the reaction mixture, or aqueous sodium sulphite, or bisulphite. Ethyl acetate can be replaced by n-butyl acetate, methyl t-butyl ether methyl ethyl ketone, methyl isobutyl ketone, and the like. Hexane can be replaced by pentane, cyclohexane, cyclopentane, heptane, petroleum ether, and the like. Brine can be composed of aqueous solutions of sodium chloride, calcium chloride, sodium sulfate, calcium sulfate, magnesium sulfate, potassium carbonate, and the like.

The reaction steps are exemplified by the Example that follows. The product of the novel process of this invention is a topically effective carbonic anhydrase inhibitor useful in the treatment of ocular hypertension. It is administered topically to the eye usually as a solution, comprising about 0.1% to 15% by weight of compound, one or two drops at a time, one to four times a day.

EXAMPLE 1

Trifluoroacetic anhydride (106 mL, 0.75 mol) was added to a solution of (S)-3-(2-thienylthio)butyric acid (113.8 g, 0.56 mol) in toluene (750 mL), which had been cooled to −5° C. Addition was done at a rate such that the temperature of the reaction mixture remained at 0°–5° C. The reaction was allowed to warm to 20°–25° C. The reaction was monitored by HPLC, and the ring closure reaction was found to be complete after 2 hours. The reaction mixture was then cooled to 0° C., and $H_2O_2$(30%;233 mL) was slowly added so that the temperature of the reaction mixture remained at 25°to 30° C. Addition of $H_2O_2$ was highly exothermic. The temperature of the reaction mixture continued to rise for one hour after addition of peroxide, and the temperature was controlled by cooling the flask with an ice bath. The reaction was allowed to run for 24 hours at 20°–25° C. The reaction mixture was then cooled to −5° C., and a saturated solution of sodium bisulfite (1500 mL $H_2O$, 180 g $Na_2SO_3$) was slowly added so as to keep the temperature below 5° C. The reaction mixture was allowed to warm to 25° C., the layers were separated, and the aqueous layer washed with toluene (500 mL). The combined organic layers were then washed with water (500 mL), and concentrated to a volume of 170 mL. Hexane (550 mL) was added, and the solution cooled to 0° C. The compound was isolated by filtration to produce 92.8 g (80% yield from the acid) of crude product. The compound was recrystallized by dissolving in isopropyl alcohol (232 mL) and heating to 75°–80° C. $H_2O$ (367 mL) was then added at a rate so as to maintain the temperature at 60°–65° C. The solution was allowed to cool to room temperature, and the compound crystallized. The solution was further cooled to 0° C., and the product was isolated by filtration. The product was washed with $H_2O$ which had been cooled to 0° C. (2×60 mL), and 84.8 g (91.5% yield for the recrystallization) of ketosulfone was isolated.

Analysis: $^1H$ NMR (CDCl$_3$) δ7.65 (d,1H,J=5.1 Hz), 7.48 (d,1H,J=5.1 Hz), 3.92 (m,1 H), 3.22 (d,2H,J=2.5 Hz), 1.56 (d,3H,J=6.9 Hz); $^{13}C$ NMR (CDCl$_3$) δ187.1, 147.2, 140.4, 131.3, 126.6, 58.4, 45.1, 12.2.

EXAMPLE 2

Scale: 0.1 gram mole to make 12.8 grams of FC4010 Stage 5 sulphone at approximately 98% strength in 58% isolated yield

| Materials | Hazard catagory | MWt | Actual Wt (g) | 100% Wt (g) | Gram Moles | Molar Ratio |
|---|---|---|---|---|---|---|
| FC4010 Stage 3 acid 20% soln. in tol. | H2 | 202 | 101 | 20.2 | 0.1 | 1.0 |
| Trifluoroacetic anhydride 99% | H2 | 210 | 25.4 | 25.2 | 0.12 | 1.2 |
| 30% w/w Hydrogen peroxide | H2 | 34 | 23.8 | 7.14 | 0.21 | 2.1 |
| 20% w/w Sodium bisulphite | H2 | 104 | 52.0 | 10.4 | 0.1 | 1.0 |
| Isopropanol | M | 60 | 30.0 | 30.0 | 0.5 | 5.0 |

A 250 ml RBQF flask fitted with PTFE paddle stirrer, short Dean & Stark (D&S) side arm leading to a double surface condenser fitted with N2 bubbler, thermometer and 50 ml dropping funnel is employed in the reaction. A dry reaction flask is purged with nitrogen and charged with FC4010 Stage 3 acid solution (101 g) and the pH checked to ensure that it is acidic (pH 4). The D&S side arm is filled with dry toluene. Vacuum (about 80–100 mm Hg) is applied and the flask contents heated to reflux and azeotropically dried. The toluene solution is cooled to 35° C. and the vacuum released with nitrogen. A slow nitrogen bleed is maintained throughout the preparation.

Trifluoroacetic anhydride (25.4 g) is charged to the dropping funnel and added dropwise to the flask contents over a period of 90 minutes whilst maintaining the temperature at 30°–35° C. The solution is held at 30°–35° C. for a further 1.0 to 1.5 hours by which time cyclization is judged to be complete by GC analysis.

The temperature is raised to 40°–45° C. (agitator speed 300 rpm) and water (1.8 g) added dropwise over 10 minutes. An exotherm occurs as the excess trifluoroacetic anhydride is hydrolyzed. 30% w/w hydrogen peroxide solution (23.8 g) is charged to the dropping funnel and added dropwise to the flask over a period of 5 hours whilst maintaining the temperature at 45°–50° C. by applying cooling as necessary (a bath temperature of 35°–40° C. is adequate to maintain the temperature). On completion of the addition the reaction mixture (now a two phase system) is stirred for a further 1.0 hour to complete the oxidation (GC shows the required product at RT 10.92 with the intermediate sulphoxide at RT 10.82).

The flask contents are cooled to ambient temperature and drowned into 20% sodium bisulphite solution (52 g) contained in a 500 ml stirred flask, whilst maintaining the temperature below 25° C. After stirring for 10 minutes the mixture is transferred to a separating funnel and the lower aqueous layer separated off. The aqueous phase is extracted with toluene (25 ml) and the combined toluene phases washed with 0.5% sodium bisulphite solution (1×50 ml) followed by water (2×50 ml). The pH of the washes are checked to ensure that the pH of the final wash is between pH4–5. More water washes are applied if necessary. The combined State 4/5 reaction yield is about 74%.

The toluene solution is charged to a dry flask and toluene distilled off under vacuum (50 mmHg) until a total of 70 g have been collected. The vacuum is released with nitrogen and the flask contents cooled to 50° C. Isopropanol (30 g) is added rapidly and the resulting solution cooled to 20° C. over 1.0 hour and then held at this temperature for 2–4 hours until crystallization is complete. The crystalline product is filtered off, washed with 15°–20° C. isopropanol (2×10 ml) and finally dried in a vacuum oven at 30°–35° C. The weight of the product was 12.78 grams (Strength–GC vs. Int. Std.=98%) and recovery from crude product was 78%.

What is claimed is:

1. A process of preparing a compound of formula IV having the structural formula:

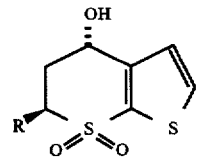

IV wherein R is hydrogen, $C_{1-4}$ alkyl, or $C_{1-4}$ alkoxy-$C_{1-4}$ alkyl, comprising adding an anhydride to a first solution containing a solvent and a compound of formula I:

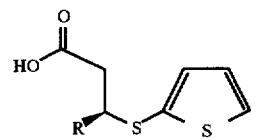

I wherein R is described as above, while maintaining a temperature of about −5° to about 50° C. to produce a second solution containing a compound of structural formula II:

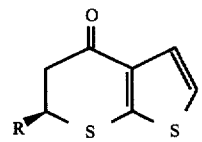

II

Wherein R is described as above, adding to the second solution from about 0.2 to about 2 equivalents of water based on the original amount of anhydride, and an oxidizing agent belonging to the group consisting of hydrogen peroxide, t-butyl hydroperoxide, periodate, perchlorate and electrochemical oxidation, while maintaining a temperature of about 15° C. to 80° C., to produce Compound III.

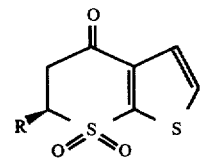

III wherein R is described as above, reducing Compound III to produce Compound IV and isolating compound IV.

2. The process of claim 1 wherein the anhydride is optionally in the presence of acids.

3. The process of claim 1 wherein R is methyl, the anhydride belongs to a group consisting of trifluoroacetic anhydride, acetic anhydride and trichloroacetic anhydride, the solvent belongs to a group consisting of toluene, benzene, cyclohexane, heptane and xylene.

4. The process of claim 3 wherein the anhydride is trifluoroacetic anhydride, the solvent is toluene and the oxidizing agent is hydrogen peroxide.

5. The process of claim 1 wherein a temperature of about 20° C. to 40° C. is maintained while the anhydride is added and the oxidizing temperature is 20° C. to about 60° C.

6. The process of claim 2 wherein the acid belongs to the group consisting of carboxylic acids and inorganic acids.

7. The process of claim 6 wherein the inorganic acids belong to the group consisting of phosphoric, polyphosphoric, orthophosphoric acids and phosphorus pentoxide.

8. The process of claim 4 wherein at least 2 mole equivalents of oxidizing agent is added.

9. A process of preparing a compound of formula IV having the structural formula:

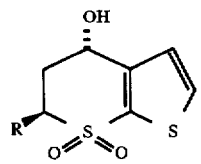

IV wherein R is methyl, comprising adding trifluoroacetic anhydride to a first solution containing toluene and a compound of formula I:

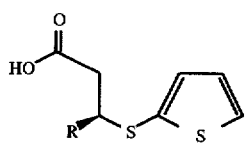

wherein R is described as above, while maintaining a temperature of about 20° to about 40° C. to produce a second solution containing a compound of structural formula II:

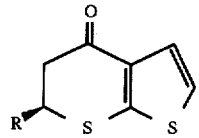

Wherein R is described as above, adding to the second solution from about 0.2 to about 2 equivalents of water based on the original amount of anhydride, and adding hydrogen peroxide, while maintaining a temperature of about 20° C. to 60° C., to produce Compound III,

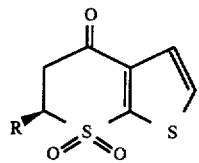

wherein R is described as above, reducing Compound III to produce Compound IV and isolating compound IV.

10. The process of claim 9 wherein the temperature is maintained at about 25° C. to 35° C. when the trifluoroacetic anhydride is added.

* * * * *

UNITED STATES PATENT AND TRADEMARK OFFICE
CERTIFICATE OF CORRECTION

PATENT NO.    : 5,760,249
DATED         : June 2, 1998
INVENTOR(S)   : David J. Mathre, Paul Sohar, David Moody and Andrew J. Blacker It is certified that error appears in the above-identified patent and that said Letters Patent is hereby corrected as shown below:

Column 2,
Line 31, delete "III" and insert -- "IV" --.

Signed and Sealed this

Third Day of December, 2002

JAMES E. ROGAN
*Director of the United States Patent and Trademark Office*